United States Patent [19]

Delahuerga et al.

[11] Patent Number: 5,088,997
[45] Date of Patent: Feb. 18, 1992

[54] GAS COAGULATION DEVICE

[75] Inventors: Louis Delahuerga, Louisville; Robert B. Stoddard; Michael S. Klicek, both of Boulder, all of Colo.

[73] Assignee: Valleylab, Inc., Boulder, Colo.

[21] Appl. No.: 494,249

[22] Filed: Mar. 15, 1990

[51] Int. Cl.$^5$ ............................................. A61B 17/39
[52] U.S. Cl. ........................................ 606/42; 606/37; 606/45; 606/49
[58] Field of Search ............... 606/41, 42, 45, 49, 606/37; 219/121.5, 121.51, 121.52

[56] References Cited

U.S. PATENT DOCUMENTS

| | | | |
|---|---|---|---|
| 3,562,486 | 2/1971 | Hatch et al. | 219/121.51 |
| 3,699,967 | 10/1972 | Anderson . | |
| 3,903,891 | 9/1975 | Brayshaw . | |
| 3,911,241 | 10/1975 | Jarrard | 606/42 |
| 3,969,603 | 7/1976 | Boughton et al. | 219/121.51 |
| 3,991,764 | 11/1976 | Incropera et al. . | |
| 4,040,426 | 8/1977 | Morrison . | |
| 4,057,064 | 11/1977 | Morrison et al. . | |
| 4,060,088 | 11/1977 | Morrison et al. . | |
| 4,123,673 | 10/1978 | Gonsea | 606/42 |
| 4,163,891 | 8/1979 | Komatsu et al. | 219/121.51 |
| 4,469,932 | 9/1984 | Spiegelberg et al. | 219/121.51 |
| 4,545,375 | 10/1985 | Cline | 606/42 |
| 4,562,838 | 1/1986 | Walker | 606/45 X |
| 4,781,175 | 11/1988 | McGreevy et al. . | |
| 4,856,514 | 8/1989 | Robinowitz et al. | 606/37 |
| 4,901,719 | 2/1990 | Trenconsky et al. . | |

Primary Examiner—Lee S. Cohen
Attorney, Agent, or Firm—Peter C. Richardson; Lawrence C. Akers; Mark Dryer

[57] ABSTRACT

A device for enhancing the safety and efficiency of a hand-operated electrosurgical pencil having an electrode with a distal end defining a tip for cutting or coagulating biological tissue, which device comprises a nose piece adapted to be mounted about said electrode and containing conduit means defining converging pathways for streams of gas which impinge obliquely on said electrode at or near the tip thereof, and electrosurgical apparatus incorporating said device and a method for coagulating or cutting biological tissue using said apparatus.

40 Claims, 7 Drawing Sheets

GAS COAGULATION DEVICE

BACKGROUND OF THE INVENTION

This invention relates to improvements in electrosurgical instruments for coagulating and cutting biological tissue. In particular, the invention relates to a device for enhancing the safety and efficiency of a hand-operated electrosurgical pencil which is used in conjunction with a flow of inert gas to perform the desired coagulation by electrosurgical fulguration or to provide electrosurgical cutting and to an improved method for performing electrosurgical operations. The invention is also concerned with an improved electrosurgical apparatus with limited current leakage for use with the said device.

Electrosurgical fulguration comprises the application of electric sparking to biological tissue, for example, human flesh or the tissue of internal organs, without significant cutting. The sparking is produced by bursts of radio-frequency electrical energy generated from an appropriate electrosurgical generator. Generally, fulguration is used to dehydrate, shrink, necrose or char the tissue, which operations are primarily to stop bleeding and oozing, or otherwise to seal the tissue. These operations are generically embraced by the term "Coagulation". Electrosurgical cutting comprises electric sparking to tissue with a cutting effect.

As used herein the term "electrosurgical pencil" is intended to mean an instrument comprising a handpiece to which is attached an electrode (the "active electrode"), which may be detachable or fixed. The pencil may be operated by a handswitch or a foot switch. The active electrode is an electrically conducting element which is usually elongated and may be in the form of a thin flat blade with a pointed or rounded distal end, or an elongated narrow cylindrical needle which may be solid or hollow with a flat, rounded, pointed or slanted distal end. Typically electrodes are known in the art as blade electrodes, loop or snare electrodes, needle electrodes and ball electrodes.

An electrosurgical pencil may be used for coagulation or cutting, or when the cutting is accompanied by hemostasis, by cutting and coagulation. The device of the present invention may be used to enhance both coagulation and cutting modes, as hereinafter described.

The handpiece of the pencil is connected to a suitable electrosurgical generator which generates the high frequency electrical energy necessary for the operation of the electrosurgical pencil. An electrosurgical generator suitable for use with electrosurgical electrodes and pencils is disclosed in U.S. Pat. No. 3,699,967, the disclosure of which is incorporated herein by reference. When an operation is performed on a patient with an electrosurgical pencil, electrical energy from the electrosurgical generator is conducted through the active electrode to the tissue at the site of the operation and then through the patient to a return electrode, placed at a convenient place on the patient's body, from whence it is returned via a patient pad or plate made of conductive material to the generator. A suitable circuit is illustrated schematically in U.S. Pat. No. 3,699,967.

The term "electrode" when used herein will generally refer to the active electrode.

The use of a stream of inert gas in conjunction with an electrosurgical electrode is known in the art. Thus, U.S. Pat. No. 4,060,088 (Morrison et al) discloses an electrosurgical method and apparatus for coagulating tissue by fulguration which involves establishing an electrical discharge in an inert gas by flowing said gas through a tubular electrode to which high-frequency electrical energy is applied.

U.S. Pat. No. 4,040,426 (Morrison) which is related to U.S. Pat. No. 4,060,088, discloses a method and apparatus wherein the inert gas flow is disposed adjacent the end of an active electrode to produce a primary electrical discharge in the gas and the apparatus includes a second electrode, electrically isolated from any source of biasing potential, which facilitates the establishment of an auxiliary electrical discharge from an electrostatic charge generated by the inert gas.

A third related U.S. Pat. No. 4,057,064 (Morrison et al) also discloses a method and apparatus for producing coagulation of tissue involving the use of a flow of inert gas and an active electrode.

The present invention provides improvements over the techniques disclosed in the above-mentioned Morrison patents, but since the basic concept of initiating an electrical discharge in an inert gas flow and the general circuitry for carrying out the procedure is a starting point for the apparatus and method of the present invention, the disclosure in each and all of the Morrison patents is incorporated herein by reference.

U.S. Pat. No. 4,781,175 discloses an electrosurgical technique for achieving coagulation involving conducting a predetermined ionizable gas not containing oxygen in a jet to tissue and conducting electrical radio-frequency energy in ionized conductible pathways in the gas jet.

Certain disadvantages present in commercially available units are overcome by the device and apparatus of the present invention.

Surprisingly, it has now been found that if at least one stream or jet of filtered inert gas is directed at a specific predetermined angle to impinge on the electrode of an electrosurgical pencil at or near the tip thereof in a device as hereinafter described the safety and efficiency of the pencil is enhanced. The pencil may be used both for cutting and coagulation, and can be made completely hand-operable; thereby increasing safety and flexibility.

SUMMARY OF THE INVENTION

In accordance with the present invention there is provided a device for enhancing the safety and efficiency of a hand-operated electrosurgical pencil having an electrode with a distal end defining a tip for cutting or coagulating biological tissue, which device comprises a nose piece having a central axis and a hollow portion extending longitudinally about said axis, which hollow portion is adapted to accommodate said electrode, said nose piece containing conduit means defining at least one pathway for gas, which at least one pathway is disposed at an angle to said central axis so that gas passing therethrough impinges obliquely on said electrode at or near to the tip thereof and means for passing inert gas at a predetermined pressure and flow rate through said at least one pathway.

The configuration of the conduit means provides an angle between the gas pathway and the central axis of the nose piece within the range of about 5° to 30°, preferably 12°, which corresponds to the angle at which the gas impinges on the electrode.

Preferably, the nose piece is part of a unit which is attached to the electrosurgical pencil. Thus, the unit may be made integral with the pencil or it may be made separately from the pencil so that the device of the invention may be used with an existing hand-switched or non-hand-switched electrosurgical pencil. The said nose piece is preferably slidably mounted on the unit, so that the point of impingement of the gas on the electrode may be adjusted as desired.

Since relatively high temperatures are generated at the tip of the electrode when performing an electrosurgical operation, the nose-piece preferably is made from a rigid high temperature resistant, electrically non-conducting material, for example a polysulfone or polycarbonate plastic.

The term hand-operated electrosurgical pencil as used herein is intended to mean an instrument which is operated by hand. Preferably, the switches which actuate or control the various functions, for example the coagulation mode or cutting mode, are hand switches located on the housing of the pencil itself and the general description herein relates to the preferred embodiment with hand switches. However, some functions may be controlled by foot switches or control mechanisms not located on the pencil itself and it is to be understood that embodiments using such alternative or additional controls are included within the generality of the term hand-operated electrosurgical pencil.

The invention also provides an electrosurgical apparatus for performing at least cutting or coagulation of biological tissue, which comprises, in combination, a hand-operated electrosurgical pencil comprising an electrode with a distal end defining a tip, means for supplying high-frequency, electrical energy from an electrosurgical generator through said electrode to said tissue and means for returning said electrical energy from said tissue to said generator to complete an electrical circuit, a controlled source of inert gas, a device attached to said electrosurgical pencil, which device comprises a nose piece having a central axis and a hollow portion extending longitudinally about said axis, which hollow portion accommodates said electrode, said nose piece containing conduit means defining at least one pathway for gas, which at least one pathway is disposed at an angle to said central axis so that gas passing therethrough impinges obliquely on said electrode at or near to the tip thereof, means for connecting said conduit means to said source of inert gas and passing filtered inert gas from said source at a predetermined pressure and flow rate through said at least one pathway.

The inert gas used in the device and apparatus of the invention is a gas which is chemically inert and is not combustible in an electrical discharge nor will it support combustion. Preferred inert gases are the noble gases, i.e. helium, neon, argon, krypton and xenon. Particularly preferred for the purposes of the present invention is an inert gas selected from helium, argon, neon, and mixtures thereof. For some applications it is possible to use nitrogen, alone or in admixture with one or more of the noble gases.

In the operation of the device according to the invention the filtered inert gas is used at a predetermined pressure and flow rate. The dimensions and configuration of the gas line and conduit means for conveying the gas are such that a preferred flow rate within the range of about 2 to 15 liters per minute (1/m) is provided by a pressure drop of approximately 1 to 13 p.s.i. This pressure drop is significantly lower than that used in existing devices and enhances the safety of the present invention.

The invention further provides a method for performing an electrosurgical operation on biological tissue with enhanced safety and efficiency which comprises making the tissue part of an electrical circuit which is closed when said operation is performed, providing at least one stream of filtered inert gas, which at least one stream is directed at an angle to impinge obliquely on an electrode of a hand-operated electrosurgical pencil at or near to the tip of said electrode, bringing the tip of the electrode in close, non-touching proximity to or in contact with said tissue so that the said electrical circuit is closed by conducting electrical energy from an electrosurgical generator through said electrode and said tissue, and thereby performing the desired electrosurgical operation.

When the electrosurgical operations is coagulation, the method is performed by directing at least one converging stream of a filtered inert gas directly on to a tip of an electrosurgical electrode, bringing said tip in close proximity to the tissue, switching on the electrosurgical generator and choosing the coagulation mode for the electrode to initiate an electrical discharge in the inert gas and produce a spark between the tip and the tissue and maintaining the spark until the desired coagulation is complete.

A typical electrosurgical generator which is used with an electrosurgical pencil to perform the method of the invention will generally provide electrical energy having a radio frequency of about 500 to 750 KHz. In the coagulation mode such an electrosurgical generator will provide an open circuit, peak to peak voltage within the range of about 1 to 10,000 V and a power output within the range of about 1 to 120 watts. If desired, the electrical circuit may include a step up transformer to increase the open circuit voltage available from the electrosurgical generator. Coagulation is preferably performed at a power output of from 20 to 120 watts. In the coagulation mode the voltage is generally sufficient to initiate an electrical discharge in the inert gas which manifests itself as a spark whose length varies according to the power of the RF electrical energy and the nature, pressure and flow rate of the inert gas. If desired, the apparatus also may include an electric booster for increasing the open circuit voltage to facilitate plasmatization of the inert gas at the onset of the coagulation mode.

When the electrosurgical operation is cutting, the method is performed by directing at least one converging stream of a filtered inert gas on to an electrosurgical electrode to impinge obliquely on said electrode at a predetermined point adjacent to but away from the tip thereof, switching on the electrosurgical generator and choosing the cut mode for the electrode, placing the tip of the electrode in contact with the tissue and drawing it across the tissue to produce the desired cutting operation.

In the cutting mode, an electrosurgical generator such as that described above will provide an open circuit, peak to peak voltage of about 1 to 6,000 Volts and a power output within the range of about 1 to 300 Watts. Cutting is preferably performed at a power output of from 30 to 150 Watts.

In the cutting mode, the open circuit voltage is generally not high enough to continuously plasmatize the inert gas and initiate and maintain an electrical discharge. Accordingly, unlike coagulation, where the operation is enhanced by the initiation of an electrical discharge, the function of the inert gas is to provide a shroud around the cutting electrode. The resulting advantages include dispersion of combustible gases around the site of the operation; reduction in the amount of eschar or charring of the tissue; blowing away gases and vapors, including smoke generated in the operation, thereby providing better visibility for the surgeon; and enhanced hemostasis.

The invention still further provides an improved electrosurgical apparatus for performing at least cutting and coagulation of biological tissue, which comprises a hand operated electrosurgical pencil comprising an electrically insulating housing and an electrode with a distal end defining a tip, means for supplying high-frequency, alternating current, electrical energy from an electrosurgical generator through said electrode to said tissue and means for returning said electrical energy from said tissue to said generator to complete an electrical circuit, switching means mounted on said housing for selecting the cut mode or the coagulating mode, said switching means being connected to an isolated low voltage, direct current circuit which provides an appropriate signal to control the generator in the cut mode or coagulating mode, respectively, whereby the generator supplies the desired high-frequency, alternating current, electrical energy to said electrode and current leakage is limited.

With existing electrosurgical generators which produce electrical energy in the radio frequency range of 500 to 750 Kilohertz, various parts of the circuitry, particularly cables, may act as antennae which tend to radiate waves in the AM radio frequency range. This spurious radiation may be translated as current leakage and when the apparatus is open circuit, such current will tend to return by the path of least resistance. If such current leakage exceeds a permissible level, it may produce a burn at a point of contact in said path. Accordingly, it is desireable to reduce the radiative parts of the apparatus as much as is reasonably possible.

It has been found that an effective way to limit current leakage is to conduct certain electrically actuated operations through an isolated low voltage, direct current circuit and the improved electrosurgical apparatus of the invention achieves the desired result by utilizing an isolated DC circuit to provide the signals to control the electrosurgical generator in the cut mode or the coagulation mode.

Preferably, the low voltage direct current is produced by a step-down transformer and diode rectifier within the generator and said isolated direct current circuit comprises a three wire cable having a distal end and a proximal end, the distal end of each of the three wires being connected to the switching means on the pencil and the proximal end of the cable terminating in a three prong plug adapted to be plugged into an appropriate socket on the apparatus. The high-frequency, alternating current circuit which supplies the electrical energy from the electrosurgical generator to the electrode preferably comprises a single wire cable having a distal end and a proximal end, said distal end being connected through an electrically conducting connection to said electrode and being electrically insulated from the rest of the pencil and said proximal end being connected through a jack to said generator.

The improved apparatus described above may be used with the device of the invention and, accordingly, the invention yet further provides an improved electrosurgical apparatus as described above which includes a device comprising a nose piece having a central axis and a hollow portion extending longitudinally about said axis, which hollow portion accommodates said electrode, said nose piece containing conduit means defining at least one pathway for gas, which at least one pathway is disposed at an angle to said central axis so that gas passing therethrough impinges obliquely on said electrode at or near the tip thereof, and means for passing filtered inert gas at a predetermined pressure and flow rate through said at least one pathway.

Preferably the nose piece of the device is part of a unit which is attached to the electrosurgical pencil and the nose piece is slidably mounted on said unit so that the point of impingement of the gas on the electrode may be adjusted as desired.

In the coagulation mode, the gas impinges substantially directly on or near the tip of the electrode, whereas in the cutting mode the impingement of the gas is at a predetermined point away from the tip of the electrode. Thus, for cutting, the nose piece is slid back from the distal end of the pencil for a predetermined distance which provides optimum cutting capability and also exposes more of the electrode which facilitates cutting and increases visibility.

BRIEF DESCRIPTION OF THE DRAWINGS

The invention will be more particularly described with reference to preferred embodiment as illustrated in the accompanying drawings, in which.

DETAILED DESCRIPTION OF THE INVENTION

Figure 1:
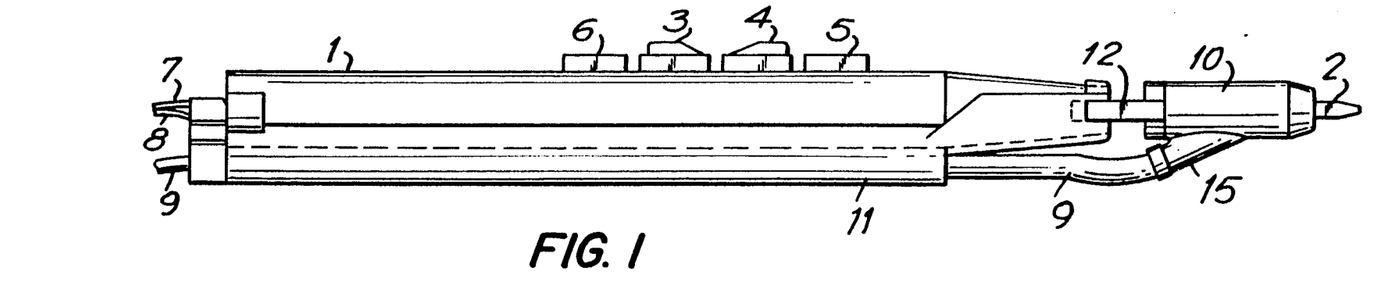
FIG. 1 is a side elevation of an apparatus according to the invention.

The apparatus illustrated in FIG. 1 of the drawings comprises an electrosurgical pencil to which is attached a device according to the invention. The pencil itself includes basic features which are present in a typical pencil known in the art. Thus, the pencil comprises a handpiece 1 to which is attached a detachable electrode 2, and the pencil is adapted to be connected to a suitable electrosurgical generator through a cable 7. The pencil is hand operated through switching means comprising button 3 for coagulation and button 4 for cutting. In the attached drawings additions and modifications have been made to the aforesaid basic features, so that FIGS. 1-20 illustrate a preferred embodiment of the device and apparatus according to the invention.

Figures 20, 21, 23:
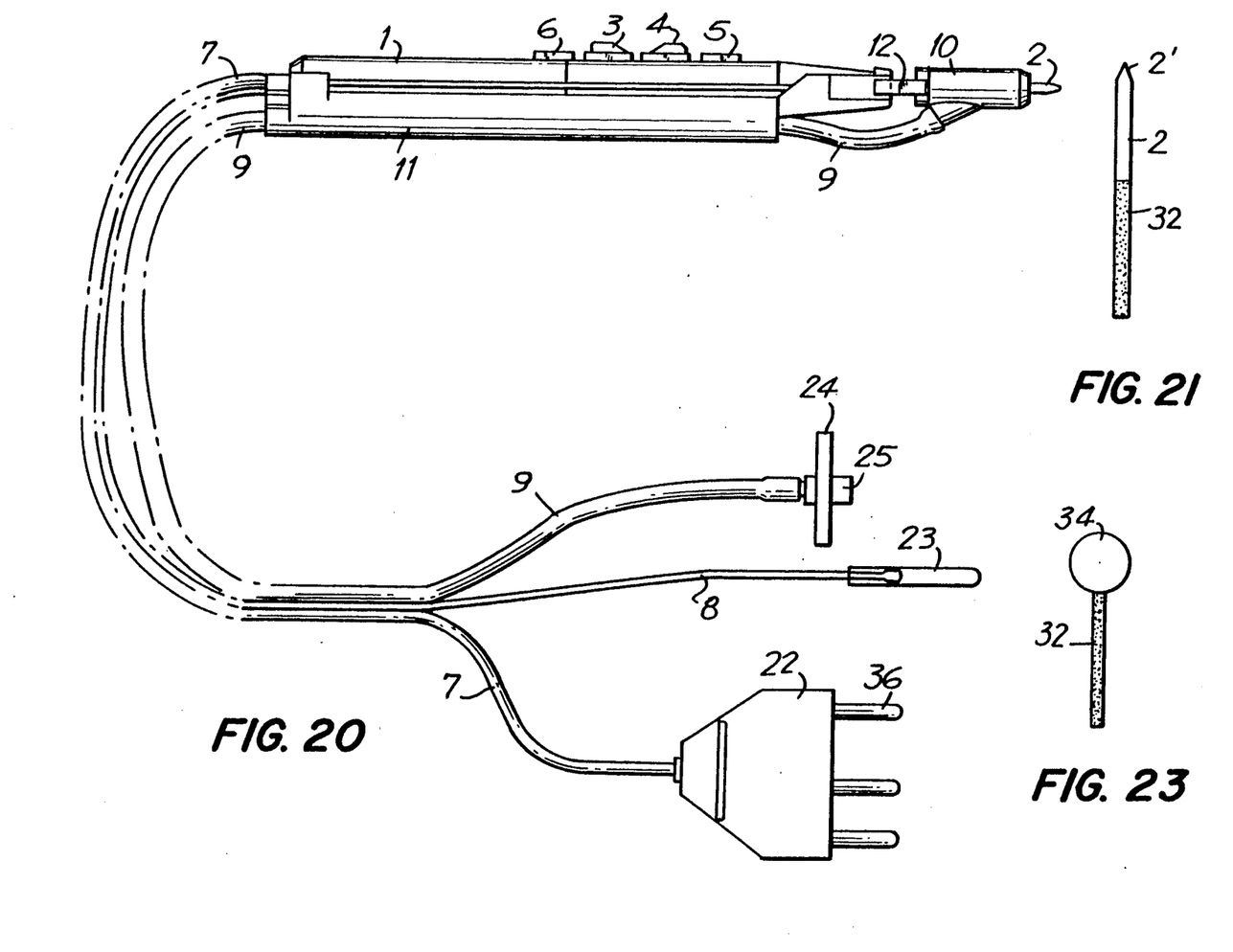
FIG. 20 is a schematic view of the cable connections to a preferred embodiment of the invention.
FIG. 21-24 illustrate profiles of various types of electrodes which may be used with the apparatus of the invention.

As shown in FIG. 1, the detachable electrode is a blade electrode and this type of electrode is shown in all the views of the preferred embodiment. A particularly preferred profile for a blade electrode is shown in FIG. 21. In this embodiment the distal end 2' of the electrode 2 converges almost to a point but the tip is slightly rounded. It has been found that an electrode with this preferred profile performs very favorably when compared, for example, with an electrode with a blunt or rounded tip. Thus, an electrode with a tip of this preferred geometry provides better control and directability of arcing. The proximal portion of the electrode has an insulation overmold 32.

Figure 22:
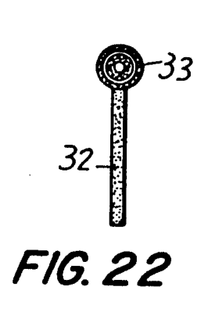
Figure 24:
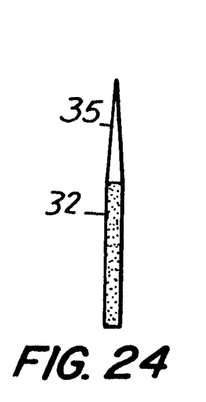

Other types of electrodes which may be used in the apparatus of the invention are illustrated in FIGS. 22-24. FIG. 22 shows a ball electrode wherein the distal end 33 is a ball or sphere of conductive material. FIG. 23 is a snare or loop electrode wherein the distal end 34 is a loop of conductive material. The snare and loop electrodes are very similar in appearance, although the manner in which each is used (known in the art) is different. FIG. 24 shows a needle electrode wherein the distal end 35 is a needle of conductive material. The needle may be hollow or solid.

It is to be understood that when electrodes having different profiles are used, the internal configuration of the nose piece of the invention may have to be modified accordingly to accommodate the different profile, as described hereinafter with reference to FIG. 11. In all cases the gas pathway is disposed at a predetermined angle to the central axis of the nose piece so that the gas impinges obliquely on the electrode at or near to the tip thereof. In the case of the ball electrode and the loop electrode the "tip" is the distal end.

Returning to FIG. 1 of the drawings, the switching means on the housing of the pencil comprises buttons not only for coagulation 3 and cutting 4, but also for turning gas flow on 5 and off 6 ("enable gas" and "disable gas"). These buttons may be used separately or in combination. Thus, the coagulation mode may be chosen with or without gas flow and likewise the cutting mode. Normally when gas flow is required the "enable gas" button 5 is pressed and then either the coagulation button 3 or the cutting button 4, as the case may be. The gas flow, at the predetermined pressure and flow rate, then comes on for a brief time, usually a few seconds, before the electrode is activated in the coagulation mode or cutting mode. This brief period of gas flow before activation of the electrode enables the surgeon to sweep the operation site with gas to remove fluid or debris without coagulation or cutting. Any such gas only period should be kept as brief as possible to avoid wastage of gas.

In some embodiments, the four buttons may be replaced by three buttons (not shown), where one button serves for both "enable gas" and "disable gas".

The connection to the apparatus is through two cables 7, 8, rather than one, although the cables may be in direct but insulated contact with each other. The first cable 7 is a three wire cable which is part of an isolated, low voltage, direct current circuit which carries signals from the switching means on the pencil to control the electrosurgical generator in the coagulating mode, when button 3 is pressed, or the cutting mode, when button 4 is pressed. The distal end of cable 7 is connected to the switching means through a printed circuit in the pencil (not shown) and the proximal end terminates in a three prong plug 22 (FIG. 20) having conductive prongs 36 and being adapted to be plugged into an appropriate outlet socket on the apparatus. The low voltage, direct current, of the order of 5 to 20 volts, is produced by a step-down transformer and diode rectifier within the apparatus and is conveyed into cable 7 through said socket. The second cable 8 is a single wire cable which carries radio frequency alternating current from the electrosurgical generator to the electrode when the apparatus is "active". The distal end of cable 8 is connected directly to the electrode through an electrically conducting connection (not shown) and is electrically insulated from the rest of the pencil. The proximal end of the cable terminates in a jack 23 (FIG. 20) for connection to the generator.

Attached to the pencil is a unit comprising a trough-shaped holder 11 (FIGS. 12-17) which preferably is made from a rigid but resilient plastic and has stiffener ribs 29, a substantially U shaped clip 30 at its proximal end and a projecting member 31 at its distal end. A device 10 is connected to said holder through slidable arms 12. A channel extending longitudinally through the base of the holder carries a gas line 9, the distal end of which is connected to a slanting inlet port 15 on device 10. As shown in FIG. 20, the proximal end of the gas line carries a filter 24 and a connector 25 which enables it to be connected to a suitable source of inert gas. The filter is necessary because the gas is used in a surgical operation and therefore must be free of particles and substantially sterile.

As used herein the term "filtered inert gas" means a gas which has been passed through a pre-sterilized filter, usually a particle membrane filter, which effectively removes contaminants and particles down to the size of a bacterium or smaller so that the resulting gas is clean and substantially sterile.

Figure 2:
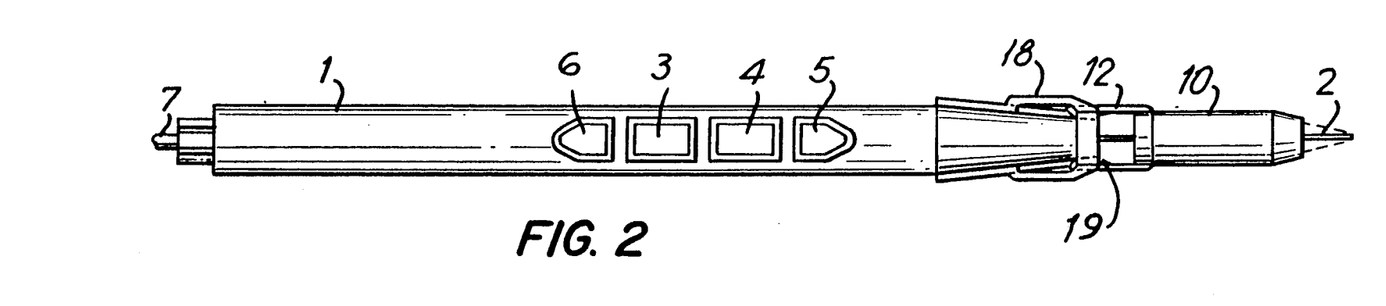
FIG. 2 is a top plan view of the apparatus illustrated in FIG. 1.
Figure 2A:
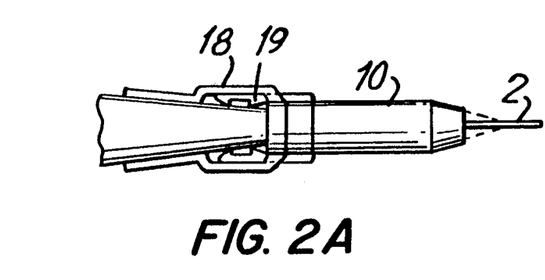
FIG. 2A is a view of the front portion of the apparatus as shown in FIG. 2 but with the nose piece in the retracted position.
Figure 3:
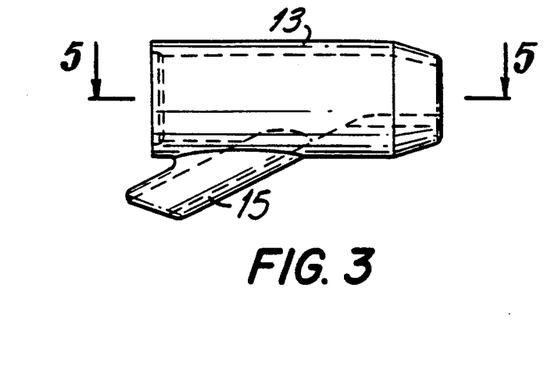
FIG. 3 is a side elevation of the outer shell of a nose piece of the invention.
Figure 4:
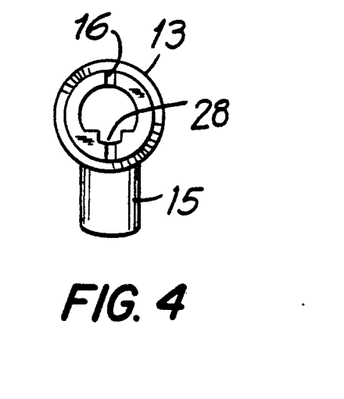
FIG. 4 is an end view of the shell of FIG. 3.
Figure 5:
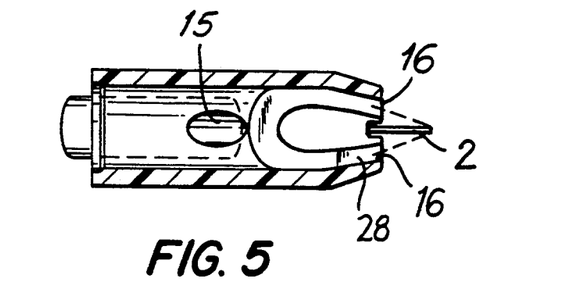
FIG. 5 is a section through lines 5—5 of FIG. 3.
Figure 6:
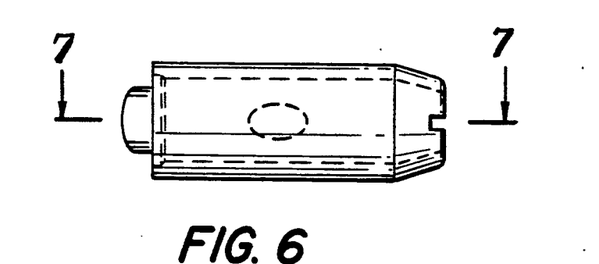
FIG. 6 is a top plan view of the shell of FIG. 3.
Figure 7:
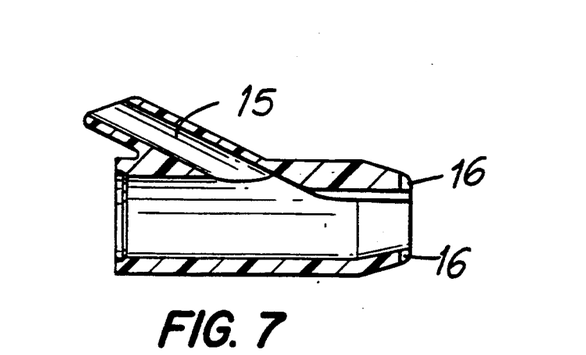
FIG. 7 is a section through lines 7—7 of FIG. 6.

When the device 10 is attached to the pencil the electrode 2 passes through a hollow portion extending longitudinally about the central axis of the nose piece comprising central slot 17 (FIG. 11) and the device may be moved backward or forward relative to the electrode. In FIG. 2 the device is in the forward position, which is the position for the coagulation mode; and in FIG. 2A the device is in the retracted position, for the cutting mode. The converging gas streams between the exit ports of the device and the points of impingement on the blade electrode are represented by dotted lines in both FIGS. 2 and 2A (as well as FIG. 9 and 10) and it will be seen that in the coagulation mode the points of impingement are substantially at the tip of the electrode;

whereas in the cutting mode the points of impingement are away from the tip. With a blade electrode, as illustrated in the drawings, the conduit means in the device of the invention provides a gas pathway comprising two converging streams which emerge from exit ports in the form of slots 16 (FIG. 11) and impinge obliquely on opposite sides of the blade. The angle between each stream of gas and the blade, which lies along the central axis of the nose piece, is preferably within the range of about 5° to 30°, and in the illustrated embodiment is about 12°.

Figure 11:
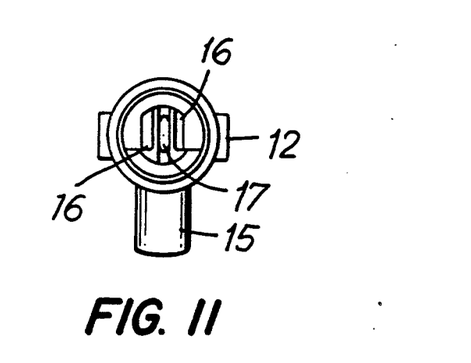
FIG. 11 is an end view of the complete nose piece.
Figure 12:
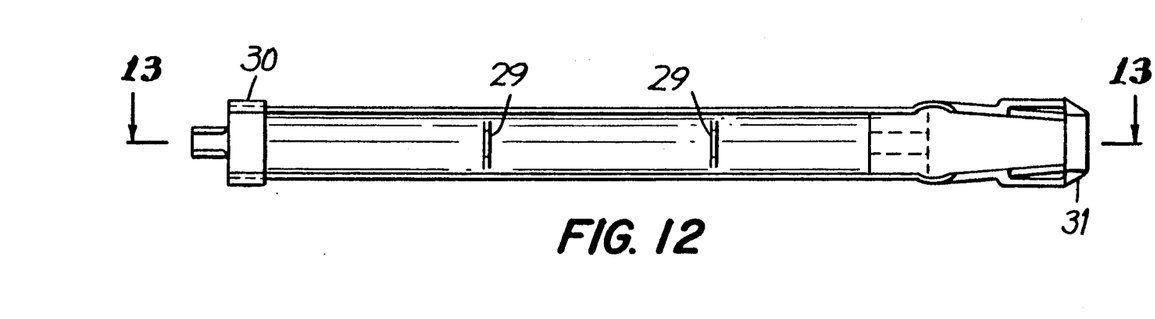
FIG. 12 is a top view of the holder part of a unit of the invention.
Figure 13:
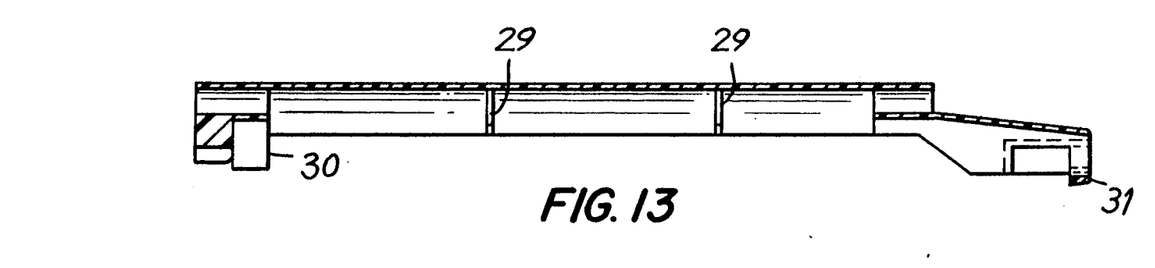
FIG. 13 is a section through lines 13—13 of FIG. 12.
Figure 14:
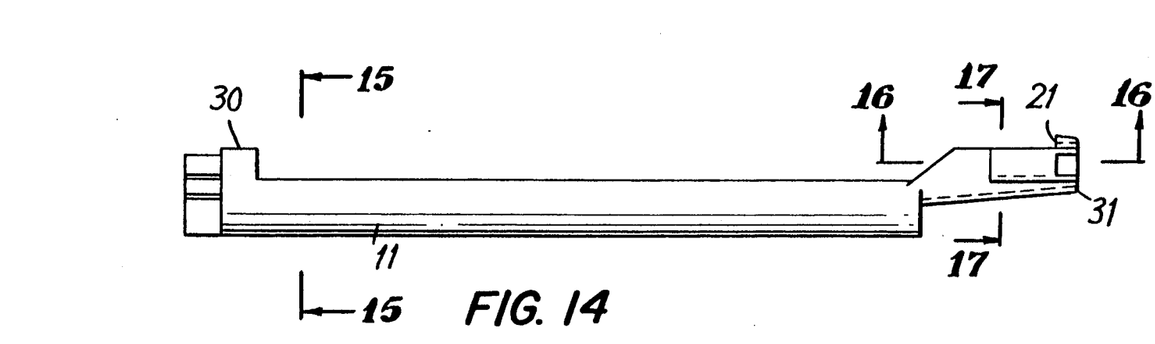
FIG. 14 is a side elevation of the holder of FIG. 12.

The angle at which the inert gas impinges on the electrode should be substantially the same for all types of electrode although the actual dimensions of the slots and exit ports as shown in FIG. 11 may require some modification to accommodate the different profiles. Thus for a loop or snare electrode the slot 17 would have to be deepened, although the exit ports 16 could remain the same. No change would be necessary in slot 17 for a ball electrode because the ball would protrude beyond the distal end of the device. However, the ports 16 would have to be displaced outwardly to achieve the correct angle of impingement. In the case of a needle electrode no modification is strictly necessary, although, if desired, the ports 16 may be merged into a single annular channel which directs the gas in a single conical stream on to the tip of the needle.

Figures 8, 9:
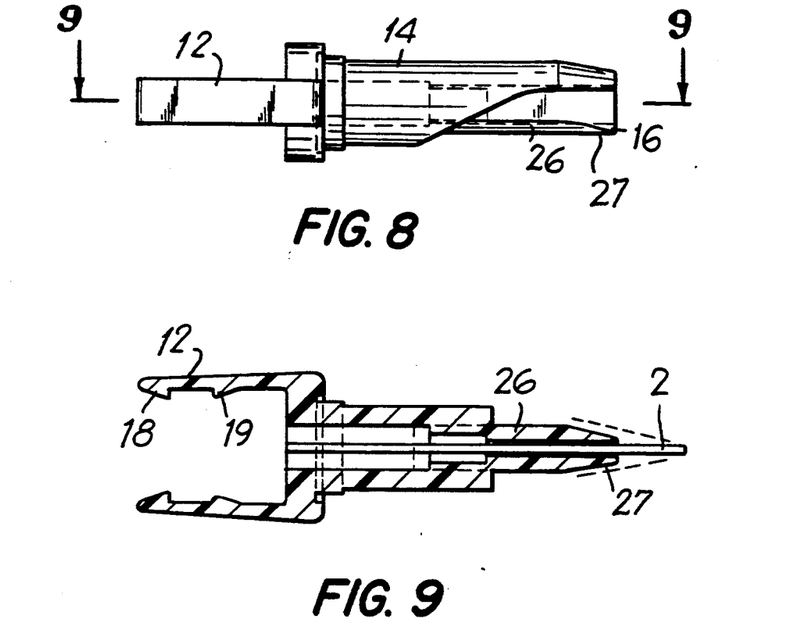
FIG. 8 is a side elevation of the core of a nose piece of the invention.
FIG. 9 is a section through line 9—9 of FIG. 8.
Figure 10:
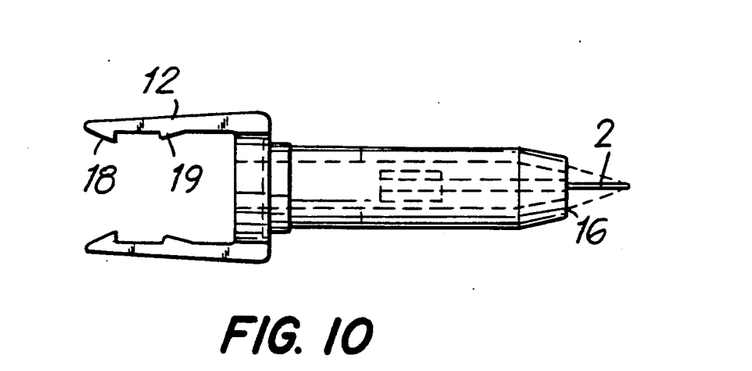
FIG. 10 is a bottom plan view of the core of FIGS. 8 and 9.

The nose cone of the device 10 illustrated in FIGS. 1, 2 and 18-20 is composed of two parts, an outer shell 13 as shown in FIG. 3-7 and an inner core 14 as shown in FIGS. 8-10.

At the base of the outer shell is a slanting inlet port 15 through which gas from line 9 (FIG. 1) enters the nose cone. When the shell is placed in locking engagement over the core the inner wall of the shell cooperates with the distal portion 26 of the core to form a conduit which provides an angled pathway for gas which exits through port 16 to impinge obliquely on the electrode 2 as shown by the dotted lines in FIGS. 5, 9 and 10. The tip of the distal portion 26 forms a key 27 which engages with a keyway 28 (FIG. 5) in the shell to provide the desired locking engagement.

The nose piece is mounted on the holder 11 through two arms 12 extending from the proximal end of the core 14. The arms pass through slots 20 located on each side of the distal end of the holder. Each of the arms has inward facing flanges adapted to butt against the inner wall 21 of the projecting member 31 at the distal end of the unit. When the rear flange 18 butts against the wall 21, the nose cone is locked in the forward position for the coagulation mode. When the front flange 19 butts against the wall 21, the nose cone is locked in the retracted position for the cutting mode. The member 31 prevents rotation of the nose cone.

Figure 15:
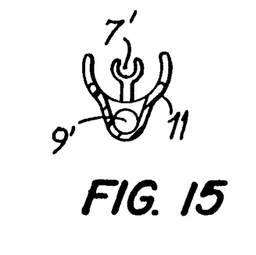
FIG. 15 is a section through lines 15—15 of FIG. 14.
Figure 16:
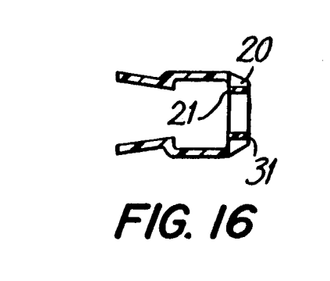
FIG. 16 is a section through lines 16—16 of FIG. 14.
Figure 17:
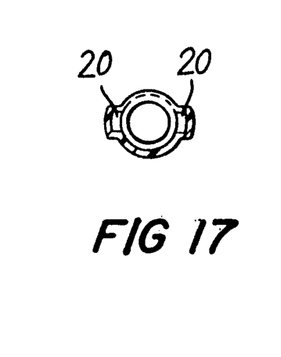
FIG. 17 is a section through lines 17—17 of FIG. 14.
Figures 18, 19:
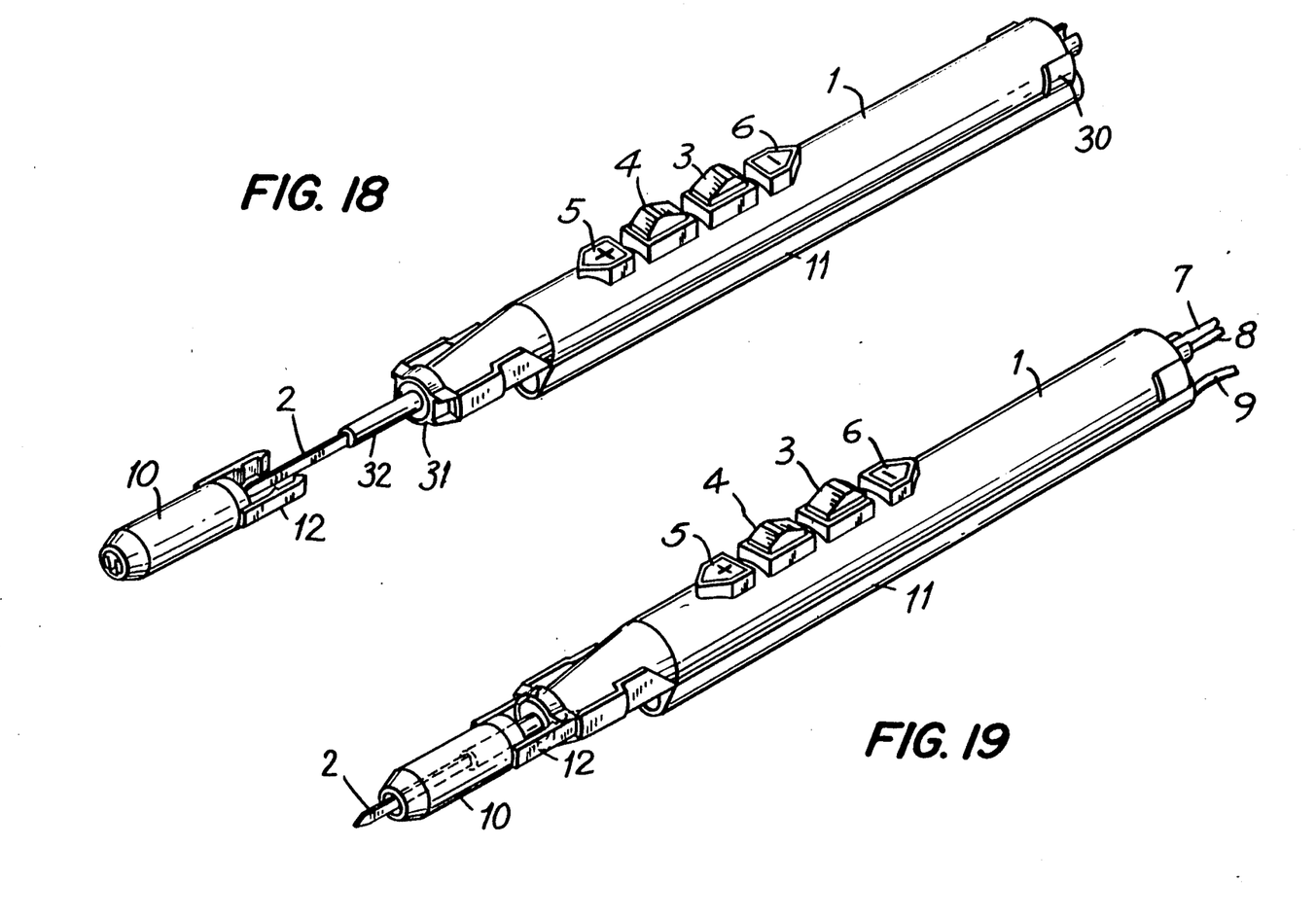
FIG. 18 is a panoramic view of the apparatus of FIGS. 1 and 2 showing the nose piece separated from the pencil.
FIG. 19 is a panoramic view of the apparatus of FIGS. 1 and 2.

FIG. 15 is a section through the holder which shows the general trough shape of the holder 11, the lower channel 9' which carries the gas line 9 and the upper channel 7' which clips around the electric cables 7, 8.

Figure 25:
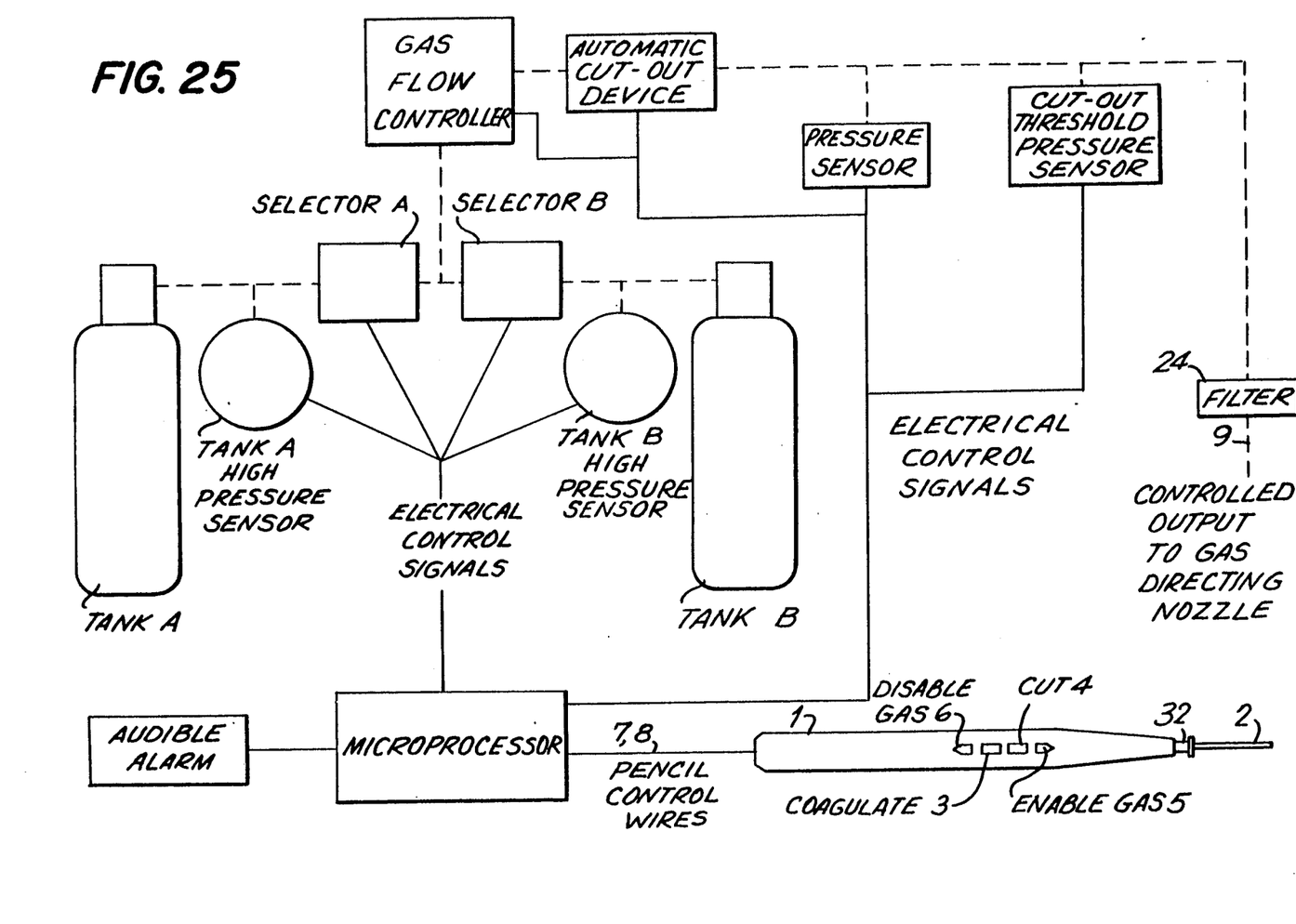
FIG. 25 is a block diagram illustrating in schematic form various features which may be incorporated in an electrosurgical system using the apparatus of the invention.

FIG. 25 is a block diagram which illustrates in schematic form an electrosurgical system incorporating the apparatus of the invention (device not shown) together with additional features which, in combination with the device of the invention, enhance the safety and efficiency of the apparatus.

The diagram particularly illustrates the juxtaposition between the various controls and sensors which may be included in the system. The individual features, i.e. sensors, microprocessor, alarm, selectors, etc, are standard items in the art and, therefore, detailed description or circuitry for each separate item is not necessary. The reference numerals given in the diagram designate the same features identified by these reference numerals in FIGS. 1-20 and the remaining features are identified by descriptive labels.

Tank A and tank B are the sources of inert gas. Each tank may contain the same inert gas as the other, for example argon, in which case one of the tanks serves as a reserve to be selected when the other tank is empty or the pressure drops to a non-usable level. Selection is made through electronically controlled selector A or selector B, as the case may be. Pressure sensors determine when the selection should be made or the selection may be made manually by control buttons.

Alternatively, tank A and tank B may each contain a different inert gas, for example, argon and helium, and selector A and selector B may be pre-set to select one or other of the said gases or a mixture thereof containing a predetermined proportion of each gas.

It is to be understood that tank A and tank B and the associated selectors and other controls are merely schematic representations of the source of inert gas, and when the system is set up to use two or more different gases, appropriate additional tanks will be included to act as reserves.

An audible alarm controlled by an appropriate electronic circuit via the microprocessor governing the selectors and pressure sensors will be actuated when the gas pressure falls below an operational level or if a fault is detected in the gas flow. The alarm also may be a visual alarm, i.e. a flashing light (not shown).

A gas flow controller, which may be operated manually, electronically, or both, controls the pressure and flow rate of the inert gas passing into the electrosurgical pencil 1 and nose piece 10 through filter 24 and gas line 9. A pressure sensor and a cut-out threshold pressure sensor monitor the gas flow and pass electrical control signals to the microprocessor. An automatic cut-out device is actuated by said signals if the gas pressure attains or exceeds a predetermined threshold.

The components illustrated in FIG. 25 in combination with the apparatus of the invention provide an electrosurgical system which is a valuable contribution to the art by virtue of at least the following advantageous characteristics:

(1) Safety: enhanced safety is provided by the hand-operated controls on the pencil, the limited current leakage circuitry and the various alarm, sensor and cut-out devices. Also the apparatus of the invention has a lower pressure drop when compared with existing devices and this lowers the risk of infusing an embolism into a patient's bloodstream.

(2) Flexibility: by varying the power of the electrical energy and the nature, pressure and flow rate of the inert gas in both the coagulation and cutting modes, different desired effects, e.g. intensity and length of spark, can be achieved.

(3) Greater control: because of the manner in which the inert gas impinges on the electrode and by choosing a suitable geometry for the electrode tip, it has been found that the apparatus of the invention provides a more cohesive and controllable spark than that achieved in prior art devices.

(4) Cost: Since the pencil is only slightly modified from standard pencils available in the art and the gas directing device is made from relatively inexpensive materials, the apparatus of the invention can be produced at a considerably lower cost than currently available gas coagulation devices.

(5) Performance: Electrosurgical pencils modified by the device of the invention provide better results, e.g. improved eschar, tissue damage, depth of necrosis and desiccation, than standard pencils (without inert gas supplementation) both in the coagulation and cutting modes. Also, in the coagulation mode, the present apparatus performs at least as well as prior art inert gas devices with respect to tissue damage and better than said devices with respect to depth of necrosis. No prior art inert gas device is known to be operable in the cutting mode.

The following tests were conducted to provide comparative data to substantiate the enhanced performance of the present apparatus over prior art devices.

Comparative Test I

Test Equipment

The following systems were used to conduct the comparative studies:
1. Prior art systems:
   a. Valleylab Force 4B electrosurgical generator serial #P9F1708B and a standard E2517 pencil.
   b. Bard Argon Beam Coagulator (ABC) 600 Serial #18316011.
2. Present invention apparatus:
   c. Valleylab Gas Coagulator with a Valleylab Force 4B electrosurgical generator serial #P9F1708B with a E2517 pencil modified into a E2522 gas coagulator handpiece. This apparatus was used in the inert gas assisted coagulation mode.

Description of Study

The study was performed on an unconditioned canine weighing 40–60 pounds. The surgical procedure was carried out with the animal under general anesthesia. Preanesthesia was obtained with Acetylpromazine 0.05 mg. per kg. (up to 3 mg. max). The anesthesia was obtained with Atropine 0.5 mg. per kg., and Pentobarbital 10–15 mg. per kg. IV supplement as needed. The animal was shaved from the chest through the abdomen. The initial incision of the animal was performed with electrosurgery to avoid unnecessary blood loss. The liver was exposed and cut using a standard scalpel to dissect completely through the tissue. This was done to expose the maximum amount of bleeding vessels. An area of at least 0.5 square inches was exposed. Hemostasis was performed by using the coagulation systems and settings listed in Table 1. For all settings, a sample of the coagulated liver tissue was removed and immediately placed into individually labelled plastic vials. These vials had an adequate amount of 10% Formalin to fully immerse the tissue samples.

TABLE 1

| SAMPLE NUMBER | TISSUE TYPE | COAGULATION SYSTEM | COAG POWER LEVEL | GAS TYPE | FLOW RATE (lpm) |
|---|---|---|---|---|---|
| 1 | Liver | Force 4B | 50 | N/A | N/A |
| 2 | Liver | Force 4B | 80 | N/A | N/A |
| 3 | Liver | Force 4B | 120 | N/A | N/A |
| 4 | Liver | Valleylab G.C. | 50 | Argon | 5 |
| 5 | Liver | Valleylab G.C. | 80 | Argon | 5 |
| 6 | Liver | Valleylab G.C. | 120 | Argon | 5 |
| 7 | Liver | Valleylab G.C. | 50 | Argon | 10 |
| 8 | Liver | Valleylab G.C. | 80 | Argon | 10 |
| 9 | Liver | Valleylab G.C. | 120 | Argon | 10 |
| 10 | Liver | Valleylab G.C. | 50 | Argon | 15 |
| 11 | Liver | Valleylab G.C. | 80 | Argon | 15 |
| 12 | Liver | Valleylab G.C. | 120 | Argon | 15 |
| 13 | Liver | Bard ABC 6000 | 50 | Argon | Preset |
| 14 | Liver | Bard ABC 6000 | 80 | Argon | Preset |
| 15 | Liver | Bard ABC 6000 | 120 | Argon | Preset |
| 16 | Liver | Bard ABC 6000 | 150 | Argon | Preset |

At the termination of the operation, the animals were euthanized with T-61 Euthanasia Solution I.V. 0.25 cc/lb. The tissue samples obtained as described in Table 1 were sectioned and prepared for the following histopathologic evaluation:
1) the average depth of necrosis of the tissue.
2) the level of damage of the tissue. This level of damage was compared against a standard (tissue sample No. 3). This standard was generated by using the Valleylab Force 4B electrosurgical generator at a Coag power level of 120 watts.

The results are shown in the following Table 2.

TABLE 2

| Sample Number | Average Depth of Necrosis mm. | Damage Relative to Sample 3 % |
|---|---|---|
| 1 | 1.9 | 90 |
| 2 | 1.6 | 90 |
| 3 (Standard) | 1.9 | 100 |
| 4 | 1.3 | 50 |
| 5 | 1.75 | 80 |
| 6 | 1.65 | 80 |
| 7 | 2.1 | 80 |
| 8 | 1.2 | 50 |
| 9 | 1.0 | 40 |
| 10 | 0.8 | 40 |
| 11 | 1.0 | 50 |
| 12 | 1.4 | 60 |
| 13 | 0.8 | 30 |
| 14 | 1.4 | 70 |
| 15 | 1.0 | 50 |
| 16 | 1.25 | 60 |

Analysis of Results

Tissue sample No. 3 was used as a standard to determine the comparative rating for the tissue damage level. tissue sample No. 3 was judged to have a damage level of 100%. The other tissue samples were compared to this standard. The average depth of necrosis for each sample was also estimated. Both quantities were entered on the Histopathology Results Form in Table 2.

The results may be summarized as follows:
1) The depth of necrosis and percent damage level are highly correlated. This implies a redundancy in the testing. Therefore, "tissue damage" will be referred to hereinafter to mean both of these quantities.

2) Fulguration with the Force 4B causes more tissue damage than the gas coagulation systems.
3) Increasing the flow rate of the Valleylab Gas Coagulator (apparatus of the invention) correlates with a decrease in tissue damage. This intuitively makes sense since a gas flow rate of zero is simple fulguration.
4) Increasing the power on any of the three systems does not strongly correlate to an increase in the damage level, as one might anticipate. A reason for this may be that the surgeon does not need to spend as much time on a particular area to achieve hemostasis if he has more power available to coagulate. In other words, the same amount of energy can be transferred to the tissue by decreasing the time but increasing the power level. This indicated that the surgeon may save time by choosing high power settings, and meanwhile not increase the damage to the tissue.
5) The data indicate that the Bard ABC and the Valleylab GC at a 15 lpm flow rate are roughly equivalent in terms of tissue damage.

COMPARATIVE TEST II

A side by side comparison to compare depth of necrosis between the Bard ABC at 150 watts and the Valleylab GC at 120 watts and 12 lpm was conducted on a single liver sample. Each device was activated on the site for 5 seconds. The sample was placed in 10% formalin for examination by the pathologist.

The average depth of necrosis with the Bard ABC was 4 mm.; and the average depth of necrosis with the Valleylab GC was 3.2 mm.

The results of the above comparative tests indicate that both gas units cause a lower level of tissue damage than a Force 4B in standard fulguration mode and the Valleylab GC unit produced less necrosis than the Bard ABC unit at each unit's highest power setting.

We claim:

1. A device for enhancing the safety and efficiency of a hand-operated electrosurgical pencil having an electrode with a distal end defining a tip for cutting or coagulating biological tissue, which device comprises a nose piece having a central axis and a hollow portion extending longitudinally about said axis, which hollow portion is adapted to accommodate said electrode, said nose piece containing conduit means defining at least one pathway for gas, which at least one pathway is disposed at an angle to said central axis so that gas passing therethrough impinges obliquely on said electrode at or near to the tip thereof and means for passing inert gas at a predetermined pressure and flow rate through said at least one pathway.

2. A device according to claim 1, in which the configuration of said conduit means provides an angle between the gas pathway and the central axis of the nose piece within the range of about 5° to 30°.

3. A device according to claim 1, in which said nose piece is part of a unit which is adapted to be attached to said electrosurgical pencil and said nose piece is slidably mounted on said unit so that the point of impingement of the gas on the electrode may be adjusted as desired.

4. A device according to claim 1, in which said nose piece is made from a rigid high temperature resistant, electrically non-conducting material.

5. A device according to claim 4, in which said material is a polysulfone or polycarbonate plastic.

6. An electrosurgical apparatus for performing at least cutting and coagulation of biological tissue, which comprises, in combination, a hand-operated electrosurgical pencil comprising an electrode with a distal end defining a tip, means for supplying high-frequency, electrical energy from a generator through said electrode to said tissue and means for returning said electrical energy from said tissue to said generator to complete an electrical circuit, a source of inert gas, a device attached to said electrosurgical pencil, which device comprises a nose piece having a central axis and a hollow portion extending longitudinally about said axis, which hollow portion accommodates said electrode, said nose piece containing conduit means defining at least one pathway for gas, which at least one pathway is disposed at an angle to said central axis so that gas passing therethrough impinges obliquely on said electrode at or near to the tip thereof, means for connecting said conduit means to said source of inert gas and passing filtered inert gas from said source at a predetermined pressure and flow rate through said at least one pathway.

7. An apparatus according to claim 6, in which said electrosurgical pencil has a handpiece having hand-operated button switches for selecting the cut mode, the coagulation mode or gas flow, separately or in combination.

8. An apparatus according to claim 6, in which the configuration of said conduit means provides an angle between the gas pathway and the central axis of the nose piece within the range of about 5° to 30°.

9. An apparatus according to claim 6, in which said nose piece is part of a unit which is attached to said electrosurgical pencil and said nose piece is slidably mounted on said unit.

10. An apparatus according to claim 9, in which said unit has a channel which carries hose means defining a gas line having a distal end and a proximal end, the distal end of said gas line being attached to said conduit means and the proximal end of said gas line being attached to filter means for removing contaminants from inert gas, a connector and control valves, said hose means, filter means, connector and control valves forming an inert gas circuit through which said conduit means is connected to said source of inert gas.

11. An apparatus according to claim 10, in which said source of inert gas provides an inert gas selected from helium, argon, neon and mixtures thereof.

12. An apparatus according to claim 10, in which the inert gas circuit comprising said hose means, filter means, connector and control valves includes pressure sensor means provided with an automatic cut-out and/or alarm which operates when the gas pressure attains or exceeds a predetermined threshold.

13. An apparatus according to claim 12, in which said inert gas circuit also includes electronic switching means for switching the hose means from one or more first sources of inert gas to one or more second sources when the pressure in said first source or sources is sufficiently low.

14. An apparatus according to claim 13, in which said switching means is associated with alarm means which operates if the gas pressure in said one or more second sources is also low or if there is any fault in the gas flow.

15. An apparatus according to claim 6, in which the electrode is detachable from the electrosurgical pencil and said electrode is a blade electrode, a loop electrode, a snare electrode, a needle electrode or a ball electrode.

16. An apparatus according to claim 6, in which the electrode is a blade made from a conductive material with a certain amount of porosity to allow a pressurized gas to flow through the blade and create a localized plasma for cutting or coagulating tissue.

17. An apparatus according to claim 6, in which said electrical circuit includes means for automatically sensing the high-frequency, electrical energy from the generator and matching the flow rate of the inert gas to the energy generated for optimum operation.

18. An apparatus according to claim 6, in which said electrical circuit includes a step up transformer for increasing the open circuit voltage available from the generator.

19. An apparatus according to claim 6, in which said electrical circuit also includes an electric booster for increasing the open circuit voltage to facilitate plasmatization of the inert gas at the onset of the coagulation mode.

20. An electrosurgical apparatus for performing at least cutting and coagulation of biological tissue, which comprises a hand operated electrosurgical pencil comprising an electrically insulating housing and an electrode with a distal end defining a tip, means for supplying high-frequency, alternating current, electrical energy from a generator through said electrode to said tissue and means for returning said electrical energy from said tissue to said generator to complete an electrical circuit, a device attached to said electrosurgical pencil, which device comprises a nose piece having a central axis and a hollow portion extending longitudinally about said central axis, which hollow portion accommodates said electrode, said nose piece containing conduit means defining at least one pathway for gas, which at least one pathway is disposed at an angle to said central axis so that gas passing therethrough impinges obliquely on said electrode at or near the tip thereof, means for passing filtered inert gas at a predetermined pressure and flow rate through said at least one pathway, and switching means mounted on said housing for selecting the cut mode or the coagulating mode, said switching means being connected to an isolated low voltage, direct current circuit which provides an appropriate signal to control the generator in the cut mode or coagulating mode, respectively, whereby the generator supplies the desired high-frequency, alternating current, electrical energy to said electrode and current leakage is limited.

21. An apparatus according to claim 20, in which low voltage direct current is produced by a step-down transformer and diode rectifier within the apparatus and said isolated direct current circuit comprises a three wire cable having a distal end and a proximal end, the distal end of each of the three wires being connected to the switching means on the pencil and the proximal end of the cable terminating in a three prong plug adapted to be plugged into an appropriate socket on the apparatus.

22. An apparatus according to claim 20, in which the high-frequency, alternating current circuit comprises a single wire cable having a distal end and a proximal end, said distal end being connected through an electrically conducting connection to said electrode and being electrically insulated from the rest of the pencil and said proximal end being connected through a jack to said generator.

23. An apparatus according to claim 20, in which the configuration of said conduit means provides an angle between the gas pathway and the central axis of the nose piece within a range of about 5° to 30°.

24. An apparatus according to claim 20, in which said nose piece is part of a unit which is attached to said electrosurgical pencil and said nose piece is slidably mounted on said unit so that the point of impingement of the gas on the electrode may be adjusted as desired.

25. An apparatus according to claim 20, in which the switching means comprises hand-operated button switches for selecting the cut mode or the coagulation mode with or without gas flow.

26. An apparatus according to claim 20, in which the nose piece is made from a high temperature resistant, electrically non-conducting material.

27. An apparatus according to claim 26, in which said material is a polysulfone or polycarbonate plastic.

28. An apparatus according to claim 24, in which said unit has a channel which carries hose means defining a gas line having a distal end and a proximal end, the distal end of said gas line being attached to said conduit means and the proximal end of said gas line being attached to filter means for removing contaminants from inert gas, a connector and control valves, said hose means, filter means, connector and control valves forming an inert gas circuit through which said conduit means is connected to said source of inert gas.

29. An apparatus according to claim 28, in which said source of inert gas provides an inert gas selected from helium, argon, neon and mixtures thereof.

30. An apparatus according to claim 28, in which the inert gas circuit comprising said hose means, filter means, connector and control valves includes pressure sensor means provided with an automatic cut-out and/or alarm which operates when the gas pressure attains or exceeds a predetermined threshold.

31. An apparatus according to claim 30, in which said inert gas circuit also includes electronic switching means for switching the hose means from one or more first sources of inert gas to one or more second sources when the pressure in said first source or sources is sufficiently low.

32. An apparatus according to claim 31, in which said switching means is associated with alarm means which operates if the gas pressure in said one or more second sources is also low or if there is any fault in the gas flow.

33. An apparatus according to claim 20, in which the electrode is detachable from the electrosurgical pencil and said electrode is a blade electrode, a loop electrode, a snare electrode, a needle electrode or a ball electrode.

34. An apparatus according to claim 20, in which the electrode is a blade made from a conductive material with a certain amount of porosity to allow a pressurized gas to flow through the blade and create a localized plasma for cutting or coagulating tissue.

35. An apparatus according to claim 20, in which said electrical circuit includes means for automatically sensing the high frequency, electrical energy from the generator and matching the flow rate of the inert gas to the energy generated for optimum operation.

36. An apparatus according to claim 20, in which the electrical circuit includes a step up transformer for increasing the open circuit voltage available from the generator.

37. An apparatus according to claim 20, in which said electrical circuit also includes an electric booster for increasing the open circuit voltage to facilitate plasmatization of the inert gas at the onset of the coagulation mode.

38. A method for performing an electrosurgical operation on biological tissue with enhanced safety and efficiency which comprises making the tissue part of an electrical circuit which is closed when said operation is performed, providing at least one stream of filtered inert gas, which at least one stream is directed at an angle to impinge obliquely on an electrode of a hand-operated electrosurgical pencil at or near to the tip of said electrode, bringing the tip of the electrode in close, non-touching proximity to or in contact with said tissue so that the said electrical circuit is closed by conducting electrical energy from an electrosurgical generator through said electrode and said tissue, and thereby performing the desired electrosurgical operation.

39. A method according to claim 38, in which said electrosurgical operation is coagulation and said coagulation is performed by directing at least one converging stream of a filtered inert gas directly on to a tip of an electrosurgical electrode, bringing said tip in close proximity to the tissue, switching on the generator and choosing the coagulation mode for the electrode to initiate an electrical discharge in the inert gas and produce a plasma between the tip and the tissue and maintaining the plasma until the desired coagulation is complete.

40. A method according to claim 38, in which said electrosurgical operation is cutting and said cutting is performed by directing at least one converging stream of a filtered inert gas on to an electrosurgical electrode to impinge obliquely on said electrode at a predetermined point adjacent to but away from the tip thereof, switching on the generator and choosing the cut mode for the electrode, placing the tip of the electrode in contact with the tissue and drawing it across the tissue to produce the desired cutting operation.

* * * * *